United States Patent [19]
Kotamäki

[11] 4,419,890
[45] Dec. 13, 1983

[54] BICYCLE ERGOMETER
[75] Inventor: Esko Kotamäki, Turku, Finland
[73] Assignee: Tunturipyörä Oy, Turku, Finland
[21] Appl. No.: 244,301
[22] Filed: Mar. 16, 1981
[51] Int. Cl.³ ............................................. G01L 5/22
[52] U.S. Cl. .................................. 73/379; 73/862.12; 272/DIG. 5
[58] Field of Search ............ 73/380, 381, 379, 862.12; 272/DIG. 5

[56] References Cited
U.S. PATENT DOCUMENTS

| | | | |
|---|---|---|---|
| 2,510,973 | 7/1946 | Guillemin | 73/381 |
| 3,192,772 | 7/1965 | Tarter | 73/379 |
| 3,967,503 | 7/1976 | Svensson | 73/379 |

FOREIGN PATENT DOCUMENTS

| | | | |
|---|---|---|---|
| 1961488 | 7/1970 | Fed. Rep. of Germany . | |
| 2319301 | 11/1974 | Fed. Rep. of Germany | 73/379 |
| 2423150 | 11/1975 | Fed. Rep. of Germany | 73/379 |
| 1288626 | 9/1972 | United Kingdom . | |

Primary Examiner—E. R. Kazenske
Assistant Examiner—Tom Noland
Attorney, Agent, or Firm—Karl F. Ross; Herbert Dubno

[57] ABSTRACT

A bicycle ergometer, where with the aid of a spring balance the braking effect of a band brake on the rim of a flywheel is measured and the braking effect may be regulated. The band, spring and indicator are normally fastened to a ball-bearing fork in the hub of the wheel, thus the tightening of the band strains the bearings. The fluctations of the indicator caused by the uneven friction and the vibrations characteristic of the spring have been reduced by a hydraulic damper. In this invention the fork has been removed. The band, spring and indicator are fastened to a weight resting on the flywheel and steered by a groove on the rim of the wheel. The mass of the weight reduces the indicator fluctuations.

1 Claim, 4 Drawing Figures

BICYCLE ERGOMETER

FIELD OF THE INVENTION

The present invention deals with a bicycle ergometer with which using a spring balance, the braking effect of a band brake on the rim of a pedal driven flywheel is measured and the braking effect can be adjusted.

BACKGROUND OF THE INVENTION

In the bicycle ergometers in use and known today the brake band of the flywheel is at each end fastened to the fork carrying the hub of the wheel via ball bearings. The spring balance is also connected to the fork and thus the indicator on the fork gives a reading of the stretching of the spring and thus of the load. The brake band tightness is adjusted by a wire, which is fastened to to the band and regulates the length of the band. Calibration of the spring balance is carried out by the aid of a weight of desired size when the ergometer is in an upright position. The fluctuations due to the unevenness of the friction of the band and the vibrations of the spring in the indicator readings, have in some types been reduced by the use of a hydraulic damper.

OBJECT OF THE INVENTION

The object of the invention is to remove the component of forces arising in the bearings of the fork when the brake band is tightened and the friction of the fluid damper which have caused inexactitude in measuring the braking effect. In the system of the invention the fork has been replaced by a weight, which rests and glides on the wheel and is guided in a groove in the wheel. Both ends of the brake band, one end through the wire regulating its length, the spring and the indicator are attached to the weight. The mass of the weight effectively reduces the fluctuations of the indicator.

SPECIFIC DESCRIPTION

Figure 1:
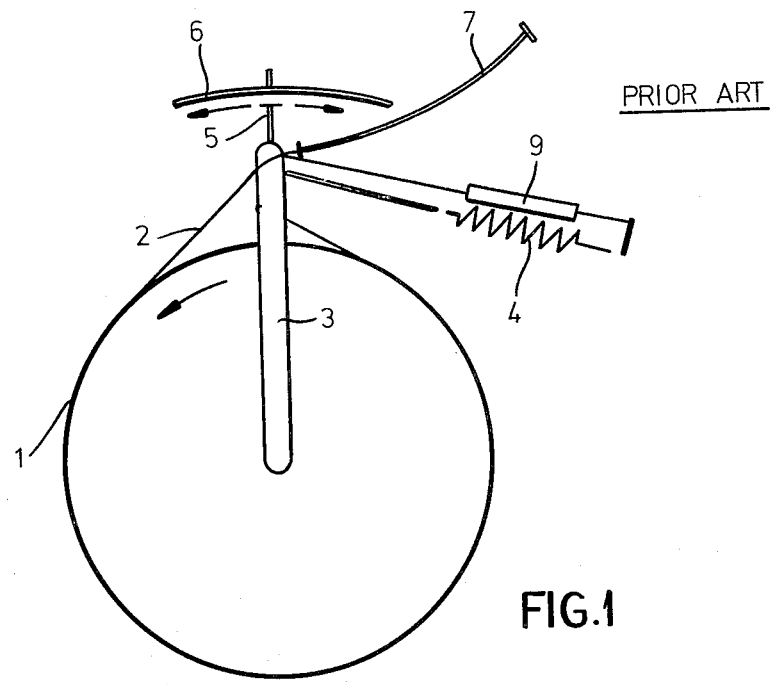
FIG. 1 is a diagrammatic side elevational view of a prior art bicycle ergometer.
Figure 2:
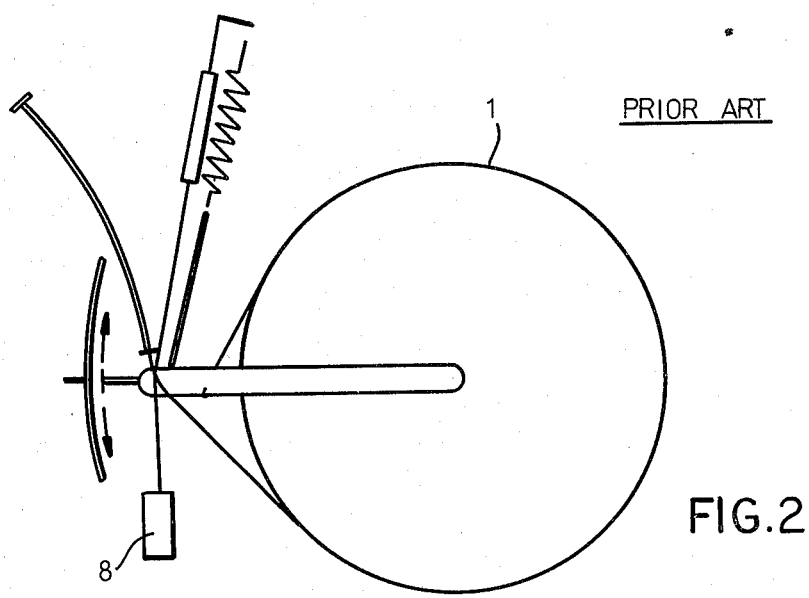
FIG. 2 is a view similar to FIG. 1 showing the ergometer of FIG. 1 in its calibrating position.

The prior art bicycle ergometers shown in FIGS. 1 and 2 comprise a fork 3 to which a flywheel 1 is journaled by bearings not shown, the flywheel 1 being surrounded by a brake band 2, one end of which is secured to the flywheel while the other end can be anchored to a wire which, when tensioned, draws the brake band against the periphery of the flywheel. When the brake band is tightened against the flywheel, the latter tends to swing in the direction of rotation of the flywheel, i.e. in the counterclockwise sense as illustrated by an arrow in FIG. 1, against the force of a spring 4 which is anchored at one end of the fork 3 and at the other end to a support (not shown). The deflection of the fork 3 is indicated by a pointer 5 on a scale 6 and represents the energy expended in driving the flywheel. The fluid damper 9 is generally provided in parallel with the spring 4 to even out the reading. The device is calibrated by suspending a known weight 8 (FIG. 2) from the fork and adjusting the spring appropriately.

This system has the aforedescribed disadvantages which result from the friction of the fluid damper and the transfer of force components to the bearing at which the fork and flywheel are mutually journaled.

Figure 3:
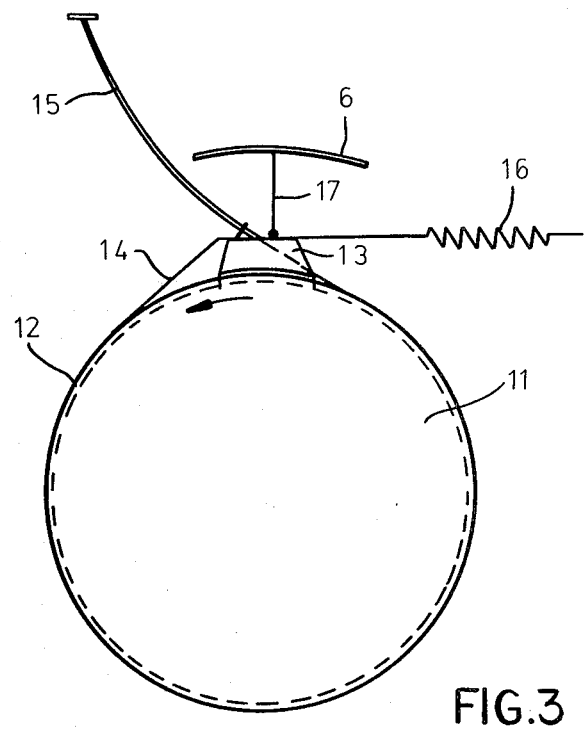
FIG. 3 is a diagrammatic elevational view showing the essential parts of a bicycle ergometer of the invention.
Figure 4:
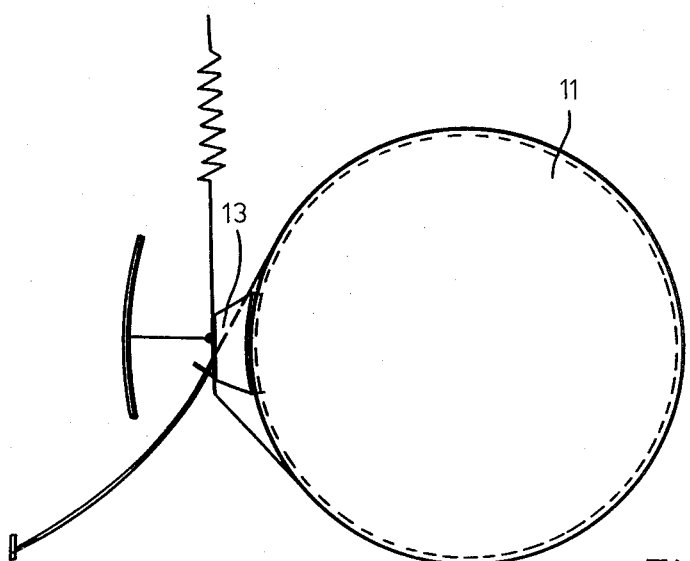
FIG. 4 is a view similar to FIG. 3 showing the latter ergometer in its calibrating position.

In FIGS. 3 and 4 I have shown an ergometer according to the invention in which the brake band 14 is not anchored to the fork, but is secured at one end to a weight 13 which, except for certain constraints would be free to ride with the flywheel 11 as the latter is rotated. The cast weight 13 is guided on the flywheel 11 by a groove 12 and carries the indicator 17 which cooperates with the scale 6.

When the wire 15 is tensioned to tighten the brake band 14 against the periphery of the wheel 11, the weight 13 is entrained with the wheel, but is retarded by the increasing force of a spring 16 anchored at one end to this weight and at its opposite end to a support (not shown).

As can be seen from FIG. 4, when the assembly is rotated through 90° from the position shown in FIG. 3, the weight 13 can act directly as a calibrating weight, thereby eliminating any need to apply a separate calibrating weight. The invention provides the following benefits:

the weight reduces the fluctuations of the indicator even better than other dampers, no ball-bearing fork at the hub of the wheel is necessary, and calibration may be carried out without additional weight; the ergometer need only be shifted into a position in which the gravitational force on the weight acts counter to the force of the spring. FIG. 4 shows this.

the braking effect is more exactly measured.

I claim:

1. A bicycle ergometer comprising:

a flywheel formed with a peripheral groove;

a brake band extending around the periphery of said flywheel;

a weight riding on the periphery of said flywheel and guided in said groove, said brake band being secured to said weight;

a tensioning element connected to said brake band for tightening same against said periphery of said flywheel;

a spring having an end connected to said weight and adapted to resist entrainment thereof with said flywheel; and an indicator connected to said weight for displaying displacement thereof against the force of said spring.

* * * * *